(12) United States Patent
Kamiguchi (10) Patent No.: US 11,369,803 B2
(45) Date of Patent: Jun. 28, 2022

(54) TREATMENT PLANNING SYSTEM

(71) Applicant: SUMITOMO HEAVY INDUSTRIES, LTD., Tokyo (JP)

(72) Inventor: Nagaaki Kamiguchi, Kanagawa (JP)

(73) Assignee: SUMITOMO HEAVY INDUSTRIES, LTD., Tokyo (JP)

( * ) Notice: Subject to any disclaimer, the term of this patent is extended or adjusted under 35 U.S.C. 154(b) by 218 days.

(21) Appl. No.: 16/661,458

(22) Filed: Oct. 23, 2019

(65) Prior Publication Data

US 2020/0121949 A1   Apr. 23, 2020

(30) Foreign Application Priority Data

Oct. 23, 2018   (JP) .............................. JP2018-199487

(51) Int. Cl.
*A61N 5/10* (2006.01)

(52) U.S. Cl.
CPC ......... *A61N 5/1031* (2013.01); *A61N 5/1049* (2013.01); *A61N 5/1065* (2013.01)

(58) Field of Classification Search
CPC .......... A61N 2005/1087; A61N 5/1031; A61N 5/103; A61N 5/1049; A61N 5/1065
See application file for complete search history.

(56) References Cited

U.S. PATENT DOCUMENTS

| 8,153,989 B2 | 4/2012 | Tachikawa et al. |
| 2005/0111621 A1* | 5/2005 | Riker ..................... G16H 70/20 378/65 |
| 2012/0264998 A1 | 10/2012 | Fujitaka et al. |
| 2013/0075622 A1 | 3/2013 | Katayose |
| 2015/0217135 A1* | 8/2015 | Bohsung ................ A61N 5/103 250/492.3 |

FOREIGN PATENT DOCUMENTS

| CN | 102743821 A | 10/2012 |
| CN | 103079641 A | 5/2013 |
| DE | 102013205876 A1 | 10/2014 |
| EP | 1378265 A1 | 1/2004 |
| JP | 2009-243891 A | 10/2009 |

OTHER PUBLICATIONS

Office Action issued in Chinese Application No. 201910971902.2, dated Apr. 6, 2021.

* cited by examiner

*Primary Examiner* — Christine H Matthews
*Assistant Examiner* — Joshua Daryl D Lannu
(74) *Attorney, Agent, or Firm* — Michael Best & Friedrich LLP (57) ABSTRACT

A treatment planning system for performing treatment planning of a charged particle beam treatment includes a calculation unit that calculates a dose distribution and an irradiation time required for the irradiation in a case where an irradiation target body is irradiated with a charged particle beam, corresponding to a plurality of predetermined cut-off dose values, and an output unit that outputs each of the cut-off values, data based on the dose distribution corresponding to each of the cut-off dose values, and the irradiation time corresponding to each of the cut-off dose values, to a display unit. The calculation unit cuts off an irradiation location having a dose which is equal to or smaller than the cut-off dose value, from doses required in respective irradiation locations of the irradiation target body, and thereafter, sets a current value of the charged particle beam when the dose distribution is calculated.

5 Claims, 8 Drawing Sheets

TREATMENT PLANNING SYSTEM

RELATED APPLICATIONS

The content of Japanese Patent Application No. 2018-199487, on the basis of which priority benefits are claimed in an accompanying application data sheet, is in its entirety incorporated herein by reference.

BACKGROUND

Technical Field

Certain embodiments of the present invention relate to a treatment planning system.

Description of Related Art

In the related art, a charged particle beam treatment apparatus is known which treats a patient by irradiating an affected site of the patient with a charged particle beam. In the related art, a charged particle beam treatment apparatus is disclosed in which an irradiation target body is divided into a plurality of layers so that each layer is scanned irradiated with the charged particle beam by using a scanning method. According to the charged particle beam treatment apparatus configured in this way irradiates the affected site with the charged particle beam, based on a treatment plan prepared by a treatment planning system.

SUMMARY

According to an embodiment of the present invention, there is provided a treatment planning system for performing treatment planning of a charged particle beam treatment. The treatment planning system includes a calculation unit that calculates a dose distribution in a case where an irradiation target body is irradiated with a charged particle beam and an irradiation time required for the irradiation, corresponding to a plurality of cut-off dose values determined in advance, and an output unit that outputs each of the cut-off values, data based on the dose distribution corresponding to each of the cut-off dose values, and the irradiation time corresponding to each of the cut-off dose values, to a display unit. The calculation unit cuts off an irradiation location having a dose which is equal to or smaller than the cut-off dose value, from doses required in respective irradiation locations of the irradiation target body, and thereafter, sets a current value of the charged particle beam when the dose distribution is calculated.

DETAILED DESCRIPTION

Here, the charged particle beam treatment apparatus as described above irradiates each layer with the charged particle beam while each layer is scanned with the charged particle beam. Consequently, a treatment time is lengthened if an irradiation time is lengthened. Therefore, in the treatment planning system, the charged particle beam treatment apparatus needs to shorten the irradiation time of the charged particle beam.

It is desirable to provide a treatment planning system which can shorten an irradiation time of a charged particle beam.

For example, in a case where the current value of the charged particle beam is set to be low with reference to a lowest dose in a map showing the dose required at each irradiation location of the irradiation target body, the irradiation location requiring a high dose is irradiated with the charged particle beam at a low scanning speed in order to lengthen the irradiation time. Accordingly, the total irradiation time of the irradiation target body is lengthened. In contrast, the calculation unit of the treatment planning system cuts off the dose which is equal to or smaller than the cut-off dose value, from the map showing the dose required at each irradiation location of the irradiation target body. Thereafter, the calculation unit sets the current value of the charged particle beam when the dose distribution is calculated. In this case, the calculation unit can set the current value, based on the dose which is higher than the cut-off dose value. In this manner, the total irradiation time can be shortened by scanning each irradiation location with the charged particle beam having a high current value. Here, the calculation unit can calculate the dose distribution in a case where the irradiation target body is irradiated with the charged particle beam and the irradiation time required for the irradiation, corresponding to the plurality of cut-off dose values determined in advance. The output unit can output each of the cut-off dose values, data based on the dose distribution corresponding to each of the cut-off dose values, and the irradiation time corresponding to each of the cut-off dose values, to the display unit. Therefore, the user can select a proper cut-off dose value while viewing a balance between irradiation accuracy and the irradiation time with reference to the display unit. According to the above-described configuration, the irradiation time of the charged particle beam can be shortened.

The treatment planning system may further include a cut-off dose value reception unit that receives the selected cut-off dose value in a case where a user selects the cut-off dose value, based on content displayed on the display unit, and a current value setting unit that sets a current value of the charged particle beam when the irradiation target body is irradiated with the charged particle beam, based on the cut-off dose value received by the cut-off dose value reception unit. In this case, treatment can be performed using the charged particle beam having the current value based on the cut-off dose value set with reference to the user's selection.

The treatment planning system may further include an input information reception unit that receives an input of a parameter based on the dose distribution from a user, and a cut-off dose value selection unit that automatically selects the cut-off dose value corresponding to a parameter closest to the parameter received by the input information reception unit. In this case, treatment can be performed using the cut-off dose value based on the parameter desired by the user.

In the treatment planning system, the calculation unit may acquire one treatment plan, and may calculate a plurality of the dose distributions in a case where a plurality of the cut-off dose values are adopted for the treatment plan. In this case, the calculation of the treatment plan can be optimized once. Accordingly, the calculation time can be shortened.

In the treatment planning system, the calculation unit may acquire a plurality of treatment plans in a case where a plurality of the cut-off dose values are adopted, and may calculate the dose distribution for each of the treatment plans. In this case, the calculation unit optimizes the treatment plan for each of the cut-off dose values. Accordingly, it is easy to suppress a disorder in the dose distribution.

According to the present invention, it is possible to provide the treatment planning system which can shorten the irradiation time of the charged particle beam.

Hereinafter, various embodiments will be described in detail with reference to the drawings. In the respective drawings, the same reference numerals will be given to the same or equivalent elements, and repeated description thereof will be omitted.

Figure 1:
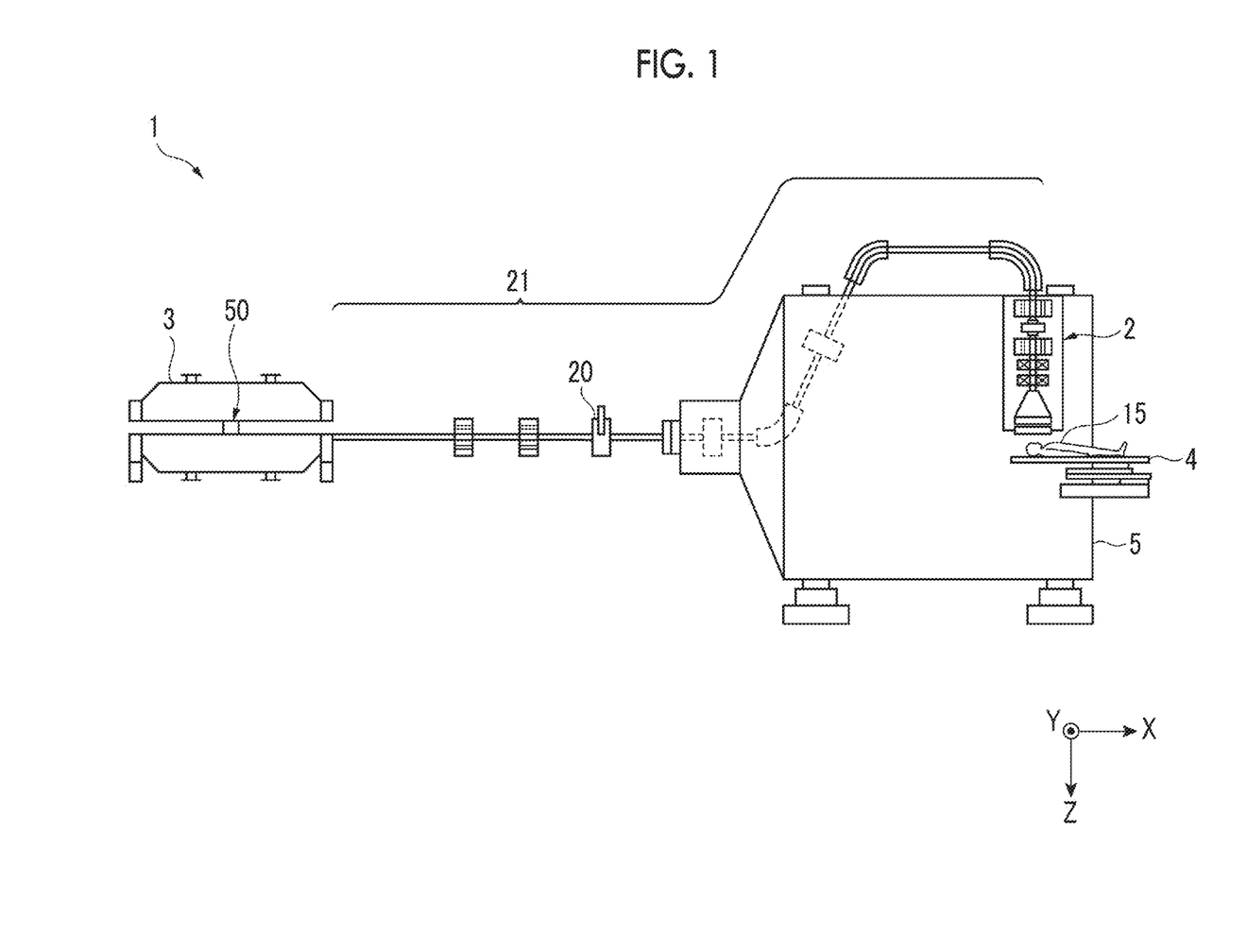
FIG. 1 is a schematic configuration diagram illustrating a charged particle beam treatment apparatus which performs a charged particle beam treatment, based on a treatment plan planned by a treatment planning system according to an embodiment of the present invention.

FIG. 1 is a schematic configuration diagram illustrating a charged particle beam treatment apparatus which performs a charged particle beam treatment, based on a treatment plan planned by a treatment planning system according to an embodiment of the present invention. A charged particle beam treatment apparatus 1 illustrated in FIG. 1 is used for a cancer treatment performed by means of radiotherapy. The charged particle beam treatment apparatus 1 includes an ion source 50 that generates a charged particle, an accelerator 3 that accelerates the charged particle generated in the ion source 50 and emits the charged particle as a charged particle beam, an irradiation unit 2 that irradiates an irradiation target body with the charged particle beam, a beam transport line 21 that transports the charged particle beam emitted from the accelerator 3 to the irradiation unit 2, and an energy adjustment unit 20 disposed between the accelerator 3 and the irradiation unit 2 on the beam transport line 21. The irradiation unit 2 is attached to a rotary gantry 5 disposed so as to surround a treatment table 4. The irradiation unit 2 is configured to be rotatable around the treatment table 4 by the rotary gantry 5.

Figure 2:
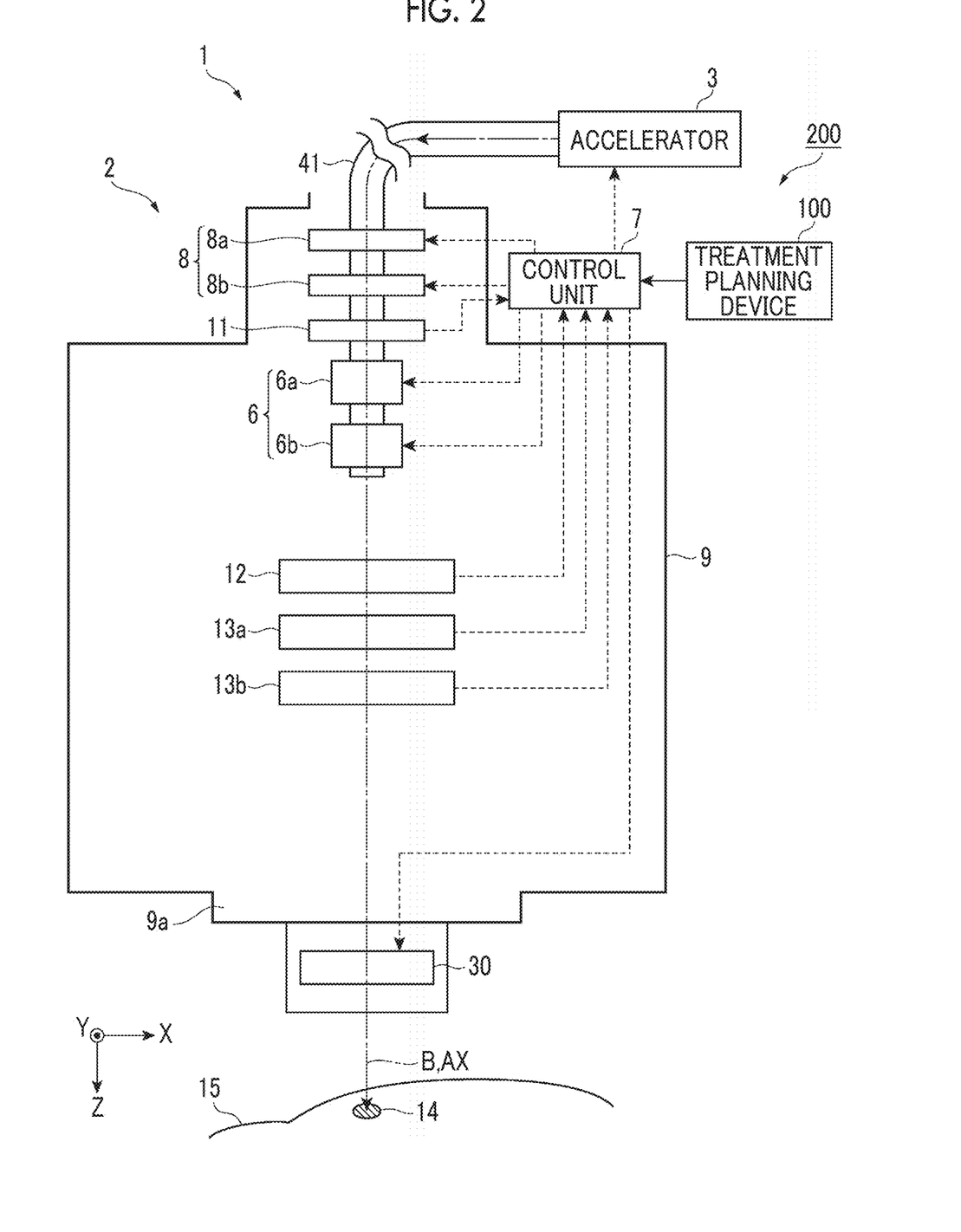
FIG. 2 is a schematic configuration diagram illustrating the vicinity of an irradiation unit of the charged particle beam treatment apparatus illustrated in FIG. 1.

FIG. 2 is a schematic configuration diagram illustrating the vicinity of an irradiation unit of the charged particle beam treatment apparatus illustrated in FIG. 1. In the following description, terms of an "X-direction", a "Y-direction", and a "Z-direction" will be used. The "Z-direction" is a direction in which a basic axis AX (irradiation axis) of a charged particle beam B extends, and is an irradiation depth direction of the charged particle beam B. The "basic axis AX" is the irradiation axis of the charged particle beam B in a case where the charged particle beam B is not deflected by an irradiation position adjustment unit 60 (to be described later). FIG. 2 illustrates a state where an irradiation target is irradiated with the charged particle beam B along the basic axis AX. The "X-direction" is one direction in a plane perpendicular to the Z-direction. The "Y-direction" is a direction perpendicular to the X-direction in a plane perpendicular to the Z-direction.

First, referring to FIG. 2, a schematic configuration of the charged particle beam treatment apparatus 1 will be described. In the following description, a case will be described where the charged particle beam treatment apparatus 1 is an irradiation apparatus relating to a scanning method. The scanning method is not particularly limited, and may adopt line scanning, raster scanning, or spot scanning. As illustrated in FIG. 2, the charged particle beam treatment apparatus 1 includes the accelerator 3, the irradiation unit 2, the beam transport line 21, and a control unit 7.

The accelerator 3 is a device which accelerates the charged particle and emits the charged particle beam B having preset energy. For example, an example of the accelerator 3 includes a cyclotron, a synchrocyclotron, and a linear accelerator. In a case where the cyclotron that emits the charged particle beam B having predetermined energy is used as the accelerator 3, the energy adjustment unit 20 is adopted. In this manner, it is possible to adjust (reduce) energy of the charged particle beam B to be supplied to the irradiation unit 2. The accelerator 3 is connected to the control unit 7, thereby controlling a current to be supplied. The charged particle beam B generated in the accelerator 3 is transported to the irradiation unit 2 by the beam transport line 21. The beam transport line 21 connects the accelerator 3, the energy adjustment unit 20, and the irradiation unit 2 to one another, and transports the charged particle beam B emitted from the accelerator 3 to the irradiation unit 2.

The irradiation unit 2 irradiates a tumor (irradiation target body) 14 located inside a body of a patient 15 with the charged particle beam B. The charged particle beam B is obtained by accelerating a charged particle at high speed, and an example thereof includes a proton beam, a heavy particle (heavy ion) ray, or a particle beam, for example. Specifically, the irradiation unit 2 irradiates the tumor 14 with the charged particle beam B which is emitted from the accelerator 3 for accelerating the charged particle generated in an ion source (not illustrated) and which is transported by the beam transport line 41. The irradiation unit 2 includes a scanning electromagnet (scanning unit) 6, a quadrupole electromagnet 8, a profile monitor 11, a dose monitor 12, flatness monitors 13a and 13b, and a degrader 30. The scanning electromagnet 6, the respective monitors 11, 12, 13a, and 13b, the quadrupole electromagnet 8, and the degrader 30 are accommodated in an irradiation nozzle 9.

The scanning electromagnet 6 includes an X-direction scanning electromagnet 6a and a Y-direction scanning electromagnet 6b. The X-direction scanning electromagnet 6a and the Y-direction scanning electromagnet 6b are respectively configured to include a pair of electromagnets, and change a magnetic field between the pair of electromagnets in response to a current supplied from the control unit 7 so that the tumor 14 is scanned with the charged particle beam B passing between the electromagnets. The X-direction scanning electromagnet 6a uses the charged particle beam B for scanning in the X-direction, and the Y-direction scanning electromagnet 6b uses the charged particle beam B for scanning in the Y-direction. The scanning electromagnets 6 are located on the basic axis AX in this order on a downstream side of the charged particle beam B from the accelerator 3.

The quadrupole electromagnet 8 includes an X-direction quadrupole electromagnet 8a and a Y-direction quadrupole electromagnet 8b. The X-direction quadrupole electromagnet 8a and the Y-direction quadrupole electromagnet 8b squeeze and converge the charged particle beam B in response to the current supplied from the control unit 7. The X-direction quadrupole electromagnet 8a converges the charged particle beam B in the X-direction, and the Y-direction quadrupole electromagnet 8b converges the charged particle beam B in the Y-direction. The current to be supplied to the quadrupole electromagnet 8 is changed, and a squeezing amount (converging amount) is changed. In this manner, a beam size of the charged particle beam B can be changed. The quadrupole electromagnet 8 is located on the basic axis AX in this order between the accelerator 3 and the scanning electromagnet 6. The beam size means a size of the charged particle beam B in an XY-plane. A beam shape means a shape of the charged particle beam B in the XY-plane.

The profile monitor 11 detects the beam shape and a position of the charged particle beam B for alignment at the time of initial setting. The profile monitor 11 is located on the basic axis AX between the quadrupole electromagnet 8 and the scanning electromagnet 6. The dose monitor 12 detects intensity of the charged particle beam B, and transmits a signal to the control unit 7. The dose monitor 12 is located on the basic axis AX on the downstream side from the scanning electromagnet 6. The flatness monitors 13a and 13b detect and monitor the beam shape and the position of the charged particle beam B. The flatness monitors 13a and 13b are located on the basic axis AX on the downstream side of the charged particle beam B from the dose monitor 12. The respective monitors 11, 12, 13a, and 13b output a detection result to the control unit 7.

The degrader 30 reduces the energy of the charged particle beam B passing therethrough, and finely adjusts the energy of the charged particle beam B. In the present embodiment, the degrader 30 is disposed in a distal portion 9a of the irradiation nozzle 9. The distal portion 9a of the irradiation nozzle 9 is an end portion on the downstream side of the charged particle beam B. The degrader 30 inside the irradiation nozzle 9 can be omitted.

For example, the control unit 7 is configured to include a CPU, a ROM, and a RAM. The control unit 7 controls the accelerator 3, the quadrupole electromagnet 8, the scanning electromagnet 6, and the degrader 30, based on detection results output from the profile monitor 11, the dose monitor 12, and the irradiation position adjustment unit 60.

The control unit 7 of the charged particle beam treatment apparatus 1 is connected to a treatment planning device 100 of a treatment planning system 200 which carries out a treatment plan for the charged particle beam treatment. Before the treatment, the treatment planning device 100 measures the tumor 14 of the patient 15 by using CT, and plans a dose distribution (dose distribution of the charged particle beam B to be used for irradiation) at each position of the tumor 14. Specifically, the treatment planning device 100 prepares a treatment plan map for the tumor 14. The treatment planning device 100 transmits the prepared treatment plan map to the control unit 7. In the treatment planning map prepared by the treatment planning device 100, which scanning path is drawn by the charged particle beam B is planned.

In a case where the tumor 14 is irradiated with the charged particle beam by using a scanning method, the tumor 14 is virtually divided into a plurality of layers in the Z-direction, and the tumor 14 in one layer is scanned and irradiated with the charged particle beam so as to follow the scanning path determined in the treatment plan. After the one layer is completely irradiated with the charged particle beam, the subsequent layer adjacent thereto is irradiated with the charged particle beam B.

In a case where the charged particle beam treatment apparatus 1 illustrated in FIG. 2 irradiates the tumor 14 with the charged particle beam B by using the scanning method, the quadrupole electromagnet 8 is brought into an operation state (ON) so as to converge the charged particle beam B passing therethrough.

Figure 3A:
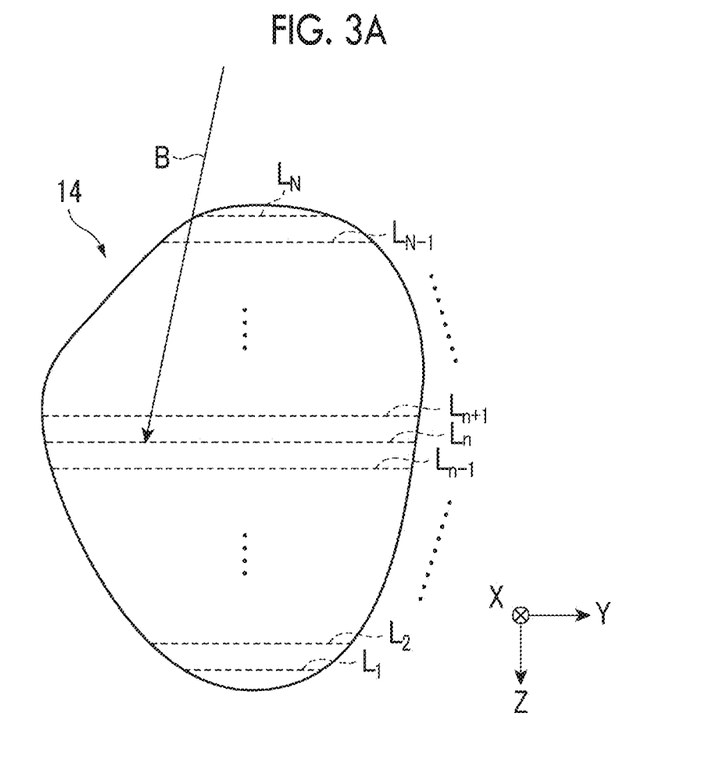
FIGS. 3A and 3B are views illustrating a layer set for a tumor.
Figure 3B:
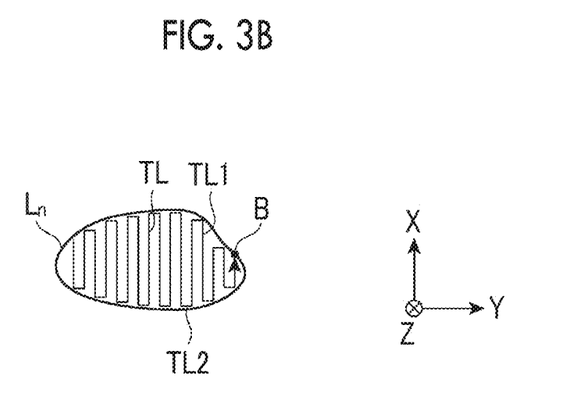

An irradiation image of the charged particle beam of the scanning electromagnet 6 in accordance with the control of the control unit 7 will be described with reference to FIGS. 3A and 3B. FIG. 3A illustrates an irradiation target body virtually sliced into the plurality of layers in the depth direction, and FIG. 3B illustrates a scanning image of the charged particle beam in one layer viewed in the depth direction.

As illustrated in FIG. 3A, the irradiation target body is virtually sliced into the plurality of layers in the depth direction of the irradiation. In this example, from the deepest layer (longest emitting range of the charged particle beam B), the irradiation target body is virtually sliced into Layer $L_1$, Layer $L_2$, . . . , Layer $L_{n-1}$, Layer $L_n$, Layer $L_{n+1}$, . . . , Layer $L_{N-1}$, Layer $L_N$, and Layer N. As illustrated in FIG. 3B, while the charged particle beam B draws a beam trajectory along a scanning path TL, the layers are continuously irradiated with the charged particle beam B along the scanning path TL of Layer $L_n$ in a case of continuous irradiation (line scanning or raster scanning). A plurality of irradiation spots of Layer $L_n$ are irradiated with the charged particle beam B in a case of spot scanning. That is, the charged particle beam B emitted from the irradiation unit 2 controlled by the control unit 7 moves on the scanning path TL.

Figure 4:
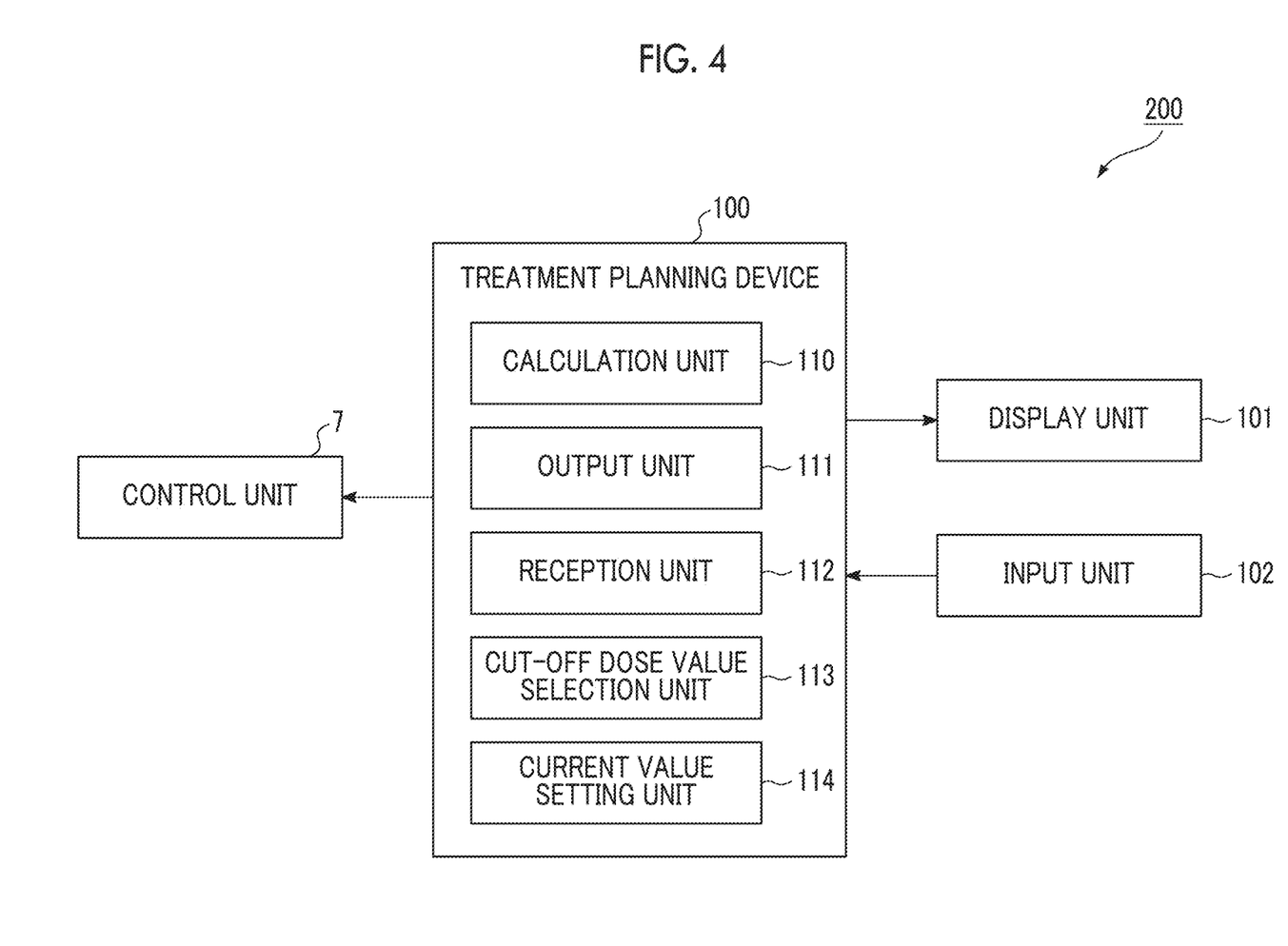
FIG. 4 is a block diagram illustrating the treatment planning system.

Next, the treatment planning system 200 will be described with reference to FIG. 4. As illustrated in FIG. 4, the treatment planning system 200 includes the treatment planning device 100, a display unit 101, and an input unit 102.

The display unit 101 displays various pieces of information for a user. The display unit 101 is configured to include a display. The display unit 101 receives a signal from the treatment planning device 100, and displays the information. The input unit 102 receives an input by an operation of the user. The input unit 102 is configured to include a mouse, a keyboard, and a touch panel.

The treatment planning device 100 includes a calculation unit 110, an output unit 111, a reception unit 112 (cut-off dose value reception unit and input information reception unit), a cut-off dose value selection unit 113, and a current value setting unit 114. The treatment planning device 100 may be configured to serve not only as a single processing device but also as a system workstation having a plurality of processing devices.

The calculation unit 110 performs various calculation processes for the treatment plan. The calculation unit 110 performs the calculation process for optimizing the number of treatment layers, operation paths, and the scanning speed, based on data relating to the tumor 14 which is acquired from CT images. The calculation unit 110 calculates the dose distribution for the optimized treatment plan.

Here, the dose of the charged particle beam B required for the tumor 14 varies depending on a location of the tumor 14. For example, the dose required in the boundary vicinity of the tumor 14 decreases, compared to the dose required in the center vicinity of the tumor 14. The charged particle beam B is used for the scanning in a state where a current value is constant. Therefore, as the scanning speed of the charged particle beam B is low, the irradiation time is lengthened. Accordingly, the dose for a specific location increases. The charged particle beam B moves at a low scanning speed for a location requiring the higher dose, and moves at a high scanning speed for a location requiring the less dose. The charged particle beam B moves at the highest scanning speed in a location requiring the least dose.

Figure 7:
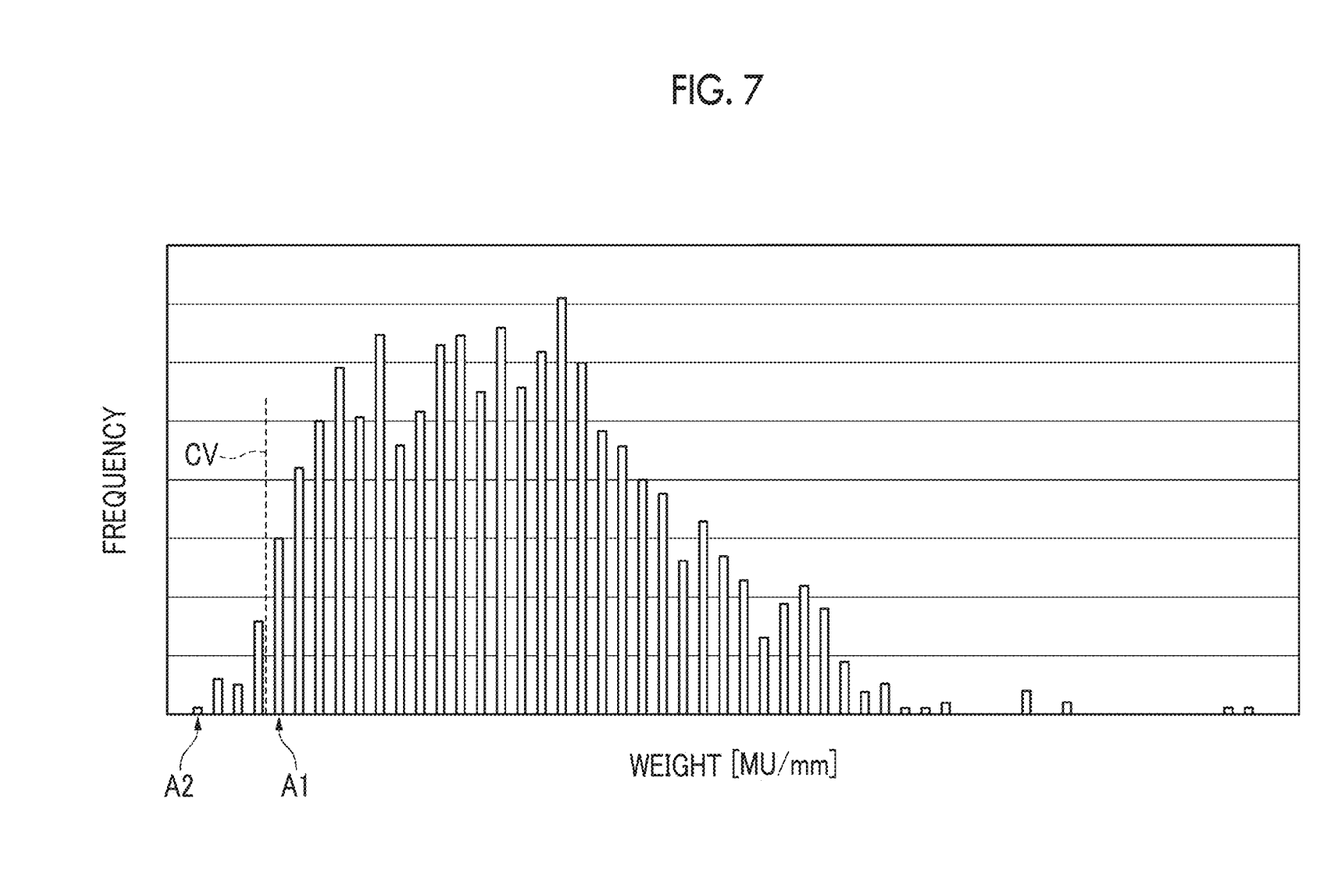
FIG. 7 is a weight map used for calculation of a calculation unit.

FIG. 7 is a weight map used for the calculation of the calculation unit 110. A horizontal axis represents a weight, and a vertical axis represents a frequency. The weight indicates the dose per unit length required at each location of the scanning path of each layer in the tumor 14. The frequency indicates how often a location having a predetermined weight is present in the scanning path of each layer of the tumor 14. The current value of the charged particle beam B is set, based on the lowest weight in the weight map. The scanning speed of the charged particle beam B is the highest scanning speed in the location having the lowest weight, and the scanning speed of the charged particle beam B is lower in the location having the higher weight.

In the present embodiment, the calculation unit 110 cuts off a low weight region from the weight map. Thereafter, as described above, the calculation unit 110 sets the current value of the charged particle beam B, and sets the scanning speed. That is, the calculation unit 110 sets a cut-off dose value ("CV" in the drawing), and cuts off the weight which is equal to or smaller than the cut-off dose value. In this case, the calculation unit 110 regards "A1" in the drawing as the lowest weight, and sets the current value of the charged particle beam B, based on the "A1". The calculation unit 110 changes the cut-off dose value to a plurality of values. In this manner, the calculation unit 110 can set the plurality of values as the current value of the charged particle beam B when the dose distribution is calculated.

The calculation unit 110 calculates the dose distribution in a case where the tumor 14 is irradiated with the charged particle beam B and the irradiation time required for the irradiation, corresponding to the plurality of cut-off dose values determined in advance. The calculation unit 110 cuts off the dose which is equal to or smaller than the cut-off dose value from the map (for example, the map illustrated in FIG. 7) indicating the dose required at each irradiation locations of the tumor 14. Thereafter, the calculation unit 110 sets the current value of the charged particle beam B when the dose distribution is calculated.

For example, the calculation unit 110 may acquire (here, prepare) one treatment plan (created here), and may calculate the plurality of dose distributions in a case where the plurality of cut-off dose values are adopted for the treatment plan. Alternatively, the calculation unit 110 may acquire (here, prepare) the plurality of treatment plans in a case where the plurality of cut-off dose values are adopted, and may calculate the dose distribution for each of the treatment plans. The calculation unit 110 calculates the irradiation time required for irradiating the whole tumor 14 for each dose distribution. That is, the calculation unit 110 calculates the time required from an irradiation start point of the layer L1 to an irradiation end point of the layer LN, in a case where the tumor 14 is irradiated with the charged particle beam B having the current value set based on the cut-off dose value while the scanning speed is changed in accordance with the dose required in each irradiation location.

The output unit 111 outputs each of the cut-off dose values, data based on the dose distribution corresponding to each of the cut-off dose values, and the irradiation time corresponding to each of the cut-off dose values, to the display unit 101. The data based on the dose distribution includes a dose volume histogram (DVH) graph and a DVH parameter.

Figure 8:
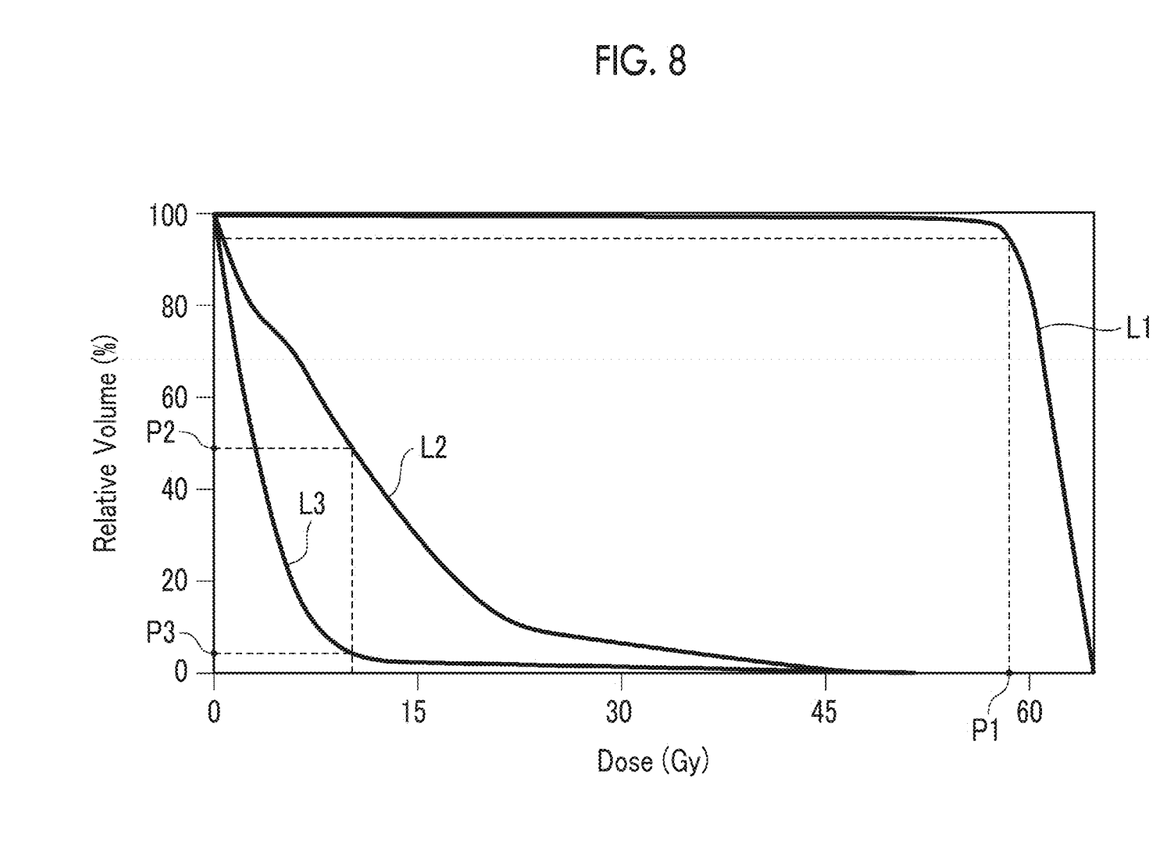
FIG. 8 is a graph illustrating a DVH.

The DVH is indicated as a graph as illustrated in FIG. 8, for example. The horizontal axis of the graph indicates the dose, and the vertical axis indicates a proportion of a volume to which the dose of the horizontal axis or more is administered, to the total volume of the irradiation target. Based on the graph, with regard to a specific dose, it is possible to recognize what percentage of the volume of the irradiation target receives the administered dose or more. For example, L1 in FIG. 8 is a graph indicating the DVH in the tumor 14 serving as the irradiation target, and L2 and L3 are graphs indicating the DVH in other organs. It is preferable that the volume for the tumor 14 is close to 100% so as to receive the higher dose. With regard to the organs which are not the irradiation target, it is preferable that the volume to which the dose is administered is as low as possible and the dose is as low as possible. If the cut-off dose value varies, a graph form of the DVH displayed on the display unit 101 also varies. In this manner, a user can select a desired cut-off dose value with reference to the graph of the DVH for each cut-off dose value, and can input the cut-off dose value to the input unit 102.

As the DVH parameter, a "dose by which the volume is a predetermined value" or a "volume for a predetermined dose" may be adopted. For example, in a case where the dose by which the volume for the tumor 14 is 95% is set as the DVH parameter, a value of the DVH parameter is a value indicated by P1 in FIG. 8. In a case where a volume for a predetermined organ with respect to a dose X is set as the DVH parameter, a value of the DVH parameter is a value indicated by P2 with regard to a graph L2 in FIG. 8, and is a value indicated by P3 with regard to a graph L3. If the cut-off dose value varies, the DVH parameter displayed on the display unit 101 also varies. In this manner, the user can select a desired cut-off dose value with reference to the DVH parameter for each cut-off dose value, and can input the cut-off dose value to the input unit 102.

The reception unit 112 receives the selected cut-off dose value in a case where the user selects the cut-off dose value, based on the content displayed on the display unit 101. The reception unit 112 receives the cut-off dose value input by the input unit 102. The reception unit 112 receives the parameter input based on the dose distribution desired by the user. That is, instead of the user determining the cut-off dose value by himself or herself, the user may input the above-described DVH parameter to the input unit 102 so that the desired dose distribution can be obtained. In this case, the reception unit 112 receives the DVH parameter input by the input unit 102.

The cut-off dose value selection unit 113 automatically selects the cut-off dose value corresponding to the DVH parameter closest to the DVH parameter received by the reception unit 112. As described above, if a certain cut-off dose value is set, a graph of the DVH corresponding thereto as illustrated in FIG. 8 is drawn. Therefore, the DVH parameter corresponding to the cut-off dose value is uniquely determined. The calculation unit 110 calculates the dose distribution corresponding to the plurality of cut-off dose values, thereby acquiring the plurality of DVH parameters. Therefore, the cut-off dose value selection unit 113 specifies the DVH parameter closest to the DVH parameter input by the user from the plurality of DVH parameters, and selects the cut-off dose value corresponding to the DVH parameter.

The current value setting unit 114 sets the current value of the charged particle beam B when the tumor 14 is irradiated with the charged particle beam B, based on the cut-off dose value received by the reception unit 112. When the calculation unit 110 calculates the dose distribution, the current value setting unit 114 sets the current value of the charged particle beam B corresponding to the cut-off dose value.

Therefore, as the current value in actual treatment, the current value setting unit 114 sets the current value corresponding to the cut-off dose value selected by the user from the current values used in calculating the dose distribution. In a case where the cut-off dose value selection unit 113 automatically selects the cut-off dose value, the current value setting unit 114 sets the current value corresponding to the cut-off current value relating to the selection, as the current value in the actual treatment.

Figure 5:
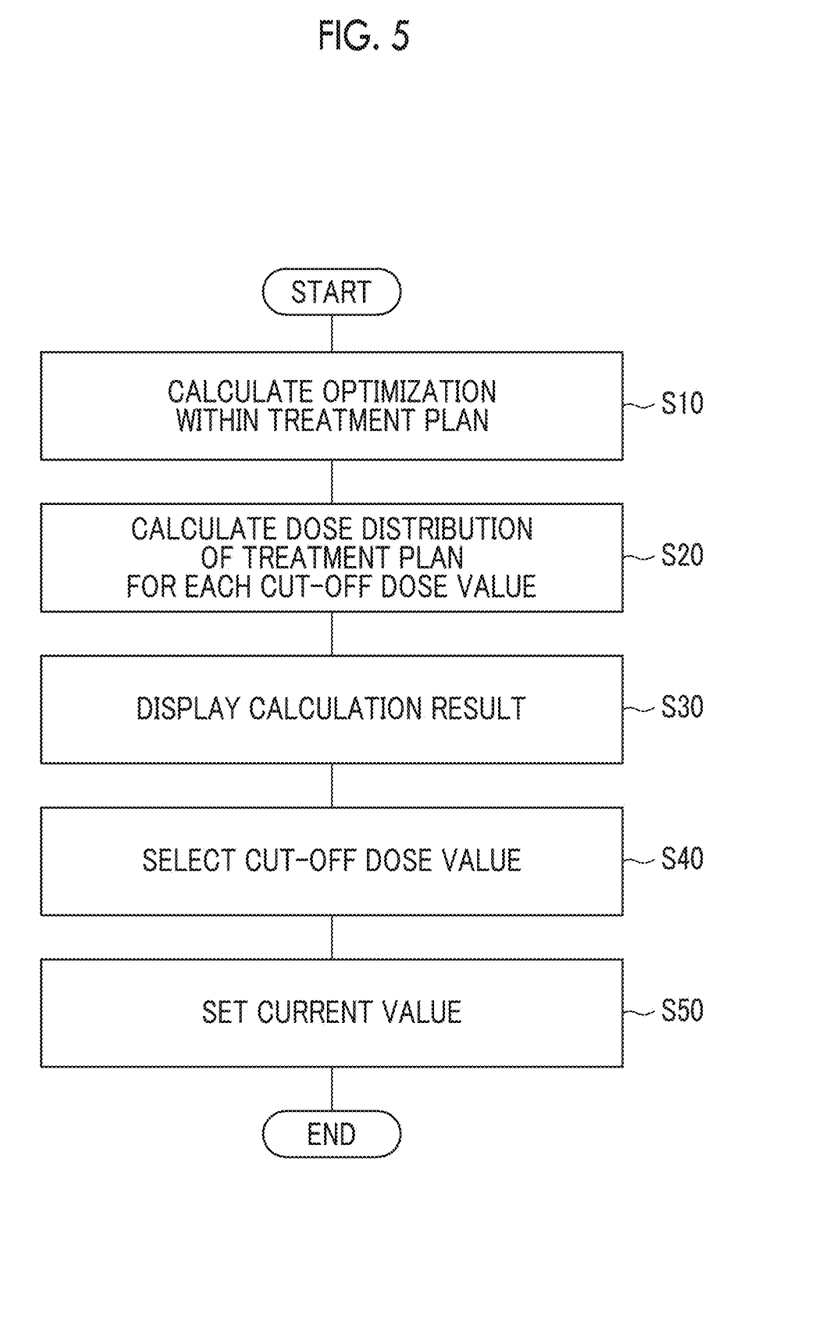
FIG. 5 illustrates an example of a procedure of the treatment plan prepared by the treatment planning system.

Next, referring to FIG. 5, an example of a procedure of the treatment plan prepared by the treatment planning system 200 according to the present embodiment will be described. As illustrated in FIG. 5, the treatment planning device 100 causes the calculation unit 110 to calculate optimization within the treatment plan (Step S10). That is, the calculation unit 110 prepares and acquires one treatment plan. Next, the treatment planning device 100 causes the calculation unit 110 to calculate the dose distribution of the treatment plan obtained in Step S10 for each cut-off dose value (Step S20). A maximum value and a minimum value of the cut-off dose value to be changed or an interval to be changed may be determined in advance, or may be selected by the user.

The treatment planning device 100 causes the output unit 111 to output each of the cut-off dose values, data based on the dose distribution corresponding to each of the cut-off dose values, and the irradiation time corresponding to each of the cut-off dose values, to the display unit 101 (Step S30). The user comprehensively determines the irradiation accuracy and the irradiation time with reference to the information displayed on the display unit 101, selects the cut-off dose value, and inputs the selected cut-off dose value to the input unit 102. The treatment planning device 100 causes the reception unit 112 to receive the cut-off dose value selected by the user in, and selects the cut-off dose value (Step S40). The treatment planning device 100 causes the current value setting unit 114 to set the current value of the charged particle beam B when the tumor 14 is irradiated with the charged particle beam B, based on the cut-off dose value selected in Step S40 (Step S50). Thereafter, the treatment planning device 100 transmits data on the prepared treatment plan to the control unit 7. According to the above-described procedure, processes illustrated in FIG. 5 are completely performed.

Figure 6:
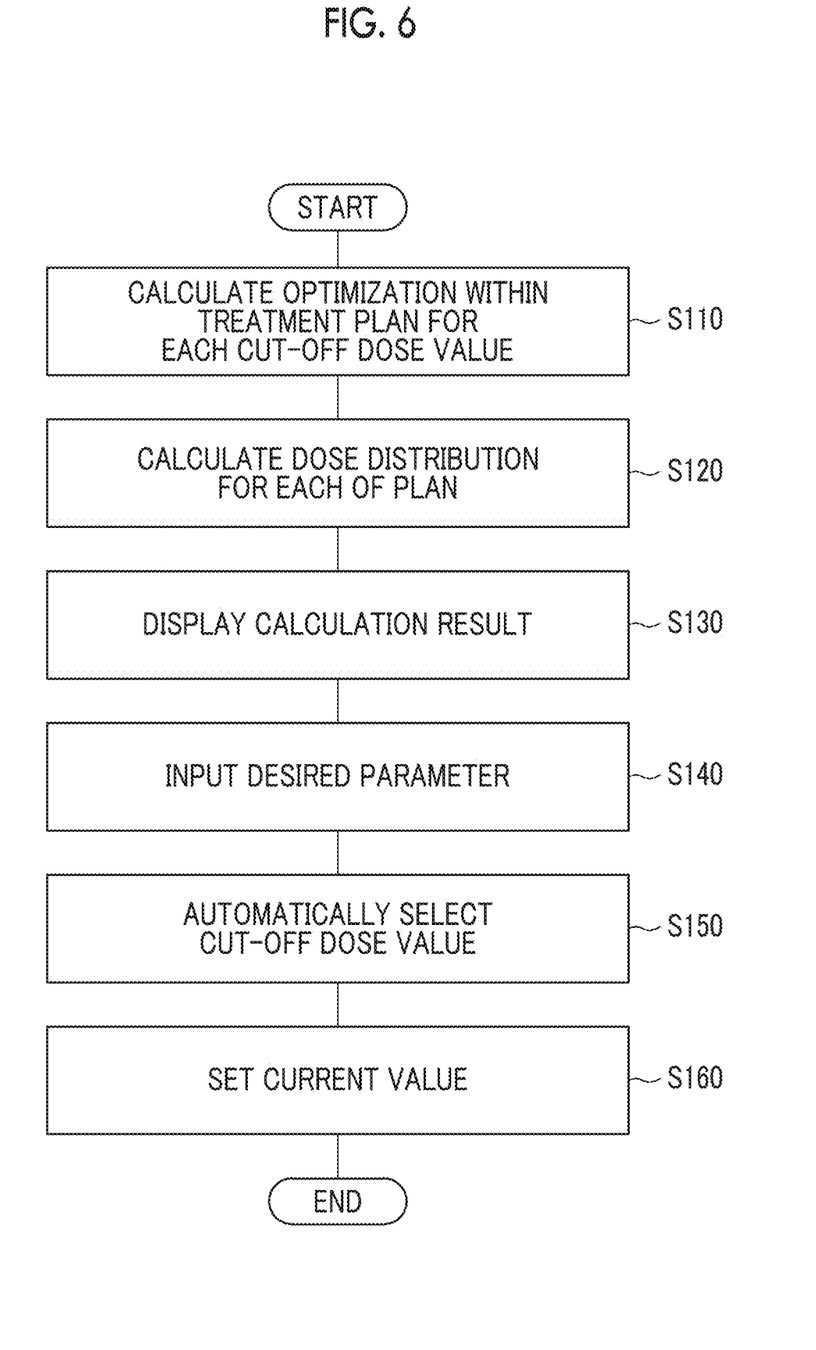
FIG. 6 illustrates another example of the procedure of the treatment plan planned by the treatment planning system.

Next, referring to FIG. 6, an example of another procedure of the treatment plan prepared by the treatment planning system 200 according to the present embodiment will be described. As illustrated in FIG. 6, the treatment planning device 100 causes the calculation unit 110 to calculate optimization within the treatment plan for each of the cut-off dose values (Step S110) That is, the calculation unit 110 prepares and acquires the plurality of treatment plans in a case where the plurality of cut-off dose values are adopted. Next, the treatment planning device 100 causes the calculation unit 110 to calculate the dose distribution for each of the treatment plans obtained in Step S110 (Step S120).

The treatment planning device 100 causes the output unit 111 to output each of the cut-off dose values, data based on the dose distribution corresponding to each of the cut-off dose values, and the irradiation time, to the display unit 101 (Step S130). The user inputs a desired DVH parameter to the input unit 102, and the treatment planning device 100 causes the reception unit 112 to receive input information input by the user (Step S140). The treatment planning device 100 automatically selects the cut-off dose value corresponding to the DVH parameter closest to the DVH parameter received by the reception unit 112 (Step S150). The treatment planning device 100 causes the current value setting unit 114 to set the current value of the charged particle beam B when the tumor 14 is irradiated with the charged particle beam B, based on the cut-off dose value selected in Step S150 (Step S160). Thereafter, the treatment planning device 100 transmits data on the prepared treatment plan to the control unit 7. According to above-described procedure, processes illustrated in FIG. 6 are completely performed. The processes in Steps S140 and S150 illustrated in FIG. 6 may be replaced with the process in Step S40 illustrated in FIG. 5. The process in Step S40 illustrated in FIG. 5 may be replaced with the process in Steps S140 and S150 illustrated in FIG. 6.

Next, operational effects of the treatment planning system 200 according to the present embodiment will be described.

First, a treatment planning system according to a comparative example will be described. The treatment planning system according to the comparative example sets the current value of the charged particle beam B, based on the lowest dose ("A2" in the drawing) from the map (refer to FIG. 7) indicating the dose required in each irradiation location of the tumor 14. Since the dose of A2 is low, the current value is set to a low value. In this case, the irradiation location requiring a high dose is irradiated with the charged particle beam at a low scanning speed. Accordingly, the irradiation time of the whole tumor 14 is lengthened.

In contrast, the calculation unit 110 of the treatment planning system 200 according to the present embodiment cuts off the dose which is equal to or smaller than the cut-off dose value from the map (refer to FIG. 7) indicating the dose required in each irradiation location of the tumor 14. Thereafter, the calculation unit 110 sets the current value of the charged particle beam B when the dose distribution is calculated. That is, the calculation unit 110 cuts off the irradiation location of the dose which is equal to or smaller than the cut-off dose value from the dose required in each irradiation location of the tumor 14. Thereafter, the calculation unit 110 sets the current value of the charged particle beam B when the dose distribution is calculated. In FIG. 7, the dose which is equal to or smaller than the cut-off dose value is cut off from the map for the sake of description. However, the map may not necessarily be used. In this case, the calculation unit 110 can set the current value, based on the dose ("A1" in FIG. 7) which is greater than the cut-off dose value. In this manner, the total irradiation time can be shortened by scanning each irradiation location with the charged particle beam having a high current value. The dose which is equal to or smaller than the cut-off dose value is less frequently used. Accordingly, even if the dose is cut off, the entire irradiation accuracy can be less affected.

Here, the calculation unit 110 can calculate the dose distribution when the tumor 14 is irradiated with the charged particle beam B, and the irradiation time required for the irradiation corresponding to the respective cut-off dose values, corresponding to the plurality of cut-off dose values determined in advance. The output unit 111 can output each of the cut-off dose values, data based on the dose distribution corresponding to each of the cut-off dose values, and the irradiation time corresponding to each of the cut-off dose values, to the display unit 101. Therefore, the user can select a proper cut-off dose value while viewing a balance between irradiation accuracy and the irradiation time with reference to the display unit 101. According to the above-described configuration, the irradiation time of the charged particle beam B can be shortened.

The treatment planning system 200 may include the reception unit 112 that receives the selected cut-off dose value in a case where the user selects the cut-off dose value, based on the content displayed on the display unit 101, and the current value setting unit 114 that sets the current value of the charged particle beam B when the tumor 14 is irradiated with the charged particle beam B, based on the cut-off dose value received by the reception unit 112. In this case, the treatment can be performed using the charged particle beam B of the current value based on the cut-off dose value set based on the user's selection.

The treatment planning system 200 includes the reception unit 112 that receives the parameter input based on the dose distribution desired by the user, and the cut-off dose value selection unit 113 that automatically selects the cut-off dose value corresponding to the DVH parameter closest to the DVH parameter received by the reception unit 112. In this case, the treatment can be performed using the cut-off dose value based on the DVH parameter desired by the user.

In the treatment planning system 200, the calculation unit 110 may acquire one treatment plan, and may calculate the plurality of dose distributions in a case where the plurality of cut-off dose values are adopted for the treatment plan. In this case, the calculation of the treatment plan can be optimized once. Accordingly, the calculation time can be shortened. The calculation of the treatment plan can be optimized once. Accordingly, the optimization of the treatment plan can be calculated outside the calculation unit 110 (by using a treatment planning device other than the treatment planning device 100).

In the treatment planning system 200, the calculation unit 110 may acquire the plurality of treatment plans in a case where the plurality of cut-off dose values are adopted, and may calculate the dose distribution for each of the treatment plans. In this case, the calculation unit 110 optimizes the treatment plan for each of the cut-off dose values. Accordingly, it is easy to suppress a disorder in the dose distribution.

The present invention is not limited to the above-described embodiment.

For example, in the above-described embodiment, the treatment planning system 200 prepares the treatment plan in which the entire region of the tumor 14 is irradiated with the charged particle beam B whose current value is set to be constant. However, a location where the current value varies may be present therein.

The calculation unit 110 of the treatment planning device 100 may be configured so that a plurality of processing devices are combined with each other. A processing device that calculates the optimization within the treatment plan (preparation of the treatment plan) and a processing device that calculates the cut-off dose value may be separately provided.

It should be understood that the invention is not limited to the above-described embodiment, but may be modified into various forms on the basis of the spirit of the invention. Additionally, the modifications are included in the scope of the invention.

What is claimed is:

1. A treatment planning system for performing treatment planning of a charged particle beam treatment, the system comprising:

a controller connected to an accelerator, wherein said accelerator is configured to accelerate a charged particle and emit a charged particle beam, and said controller is configured to control a current to be supplied to the accelerator: and a treatment planning device configured to:

calculate, in a case where an irradiation target body is irradiated with a charged particle beam, a dose distribution and an irradiation time required for the irradiation which correspond to a plurality of cut-off dose values determined in advance, output each of the cut-off dose values, data based on the dose distribution corresponding to each of the cut-off dose values, and the irradiation time corresponding to each of the cut-off dose values, to a display, and receive a selected cut-off dose value, which is selected from among the plurality of the cut-off dose values and is input by a user via an input device, and an input of a parameter based on the dose distribution, which is input by the user via the input device, the selected cut-off dose value being selected on a basis of the parameter, wherein the treatment planning device is configured to cut off an irradiation location having a dose which is equal to or smaller than the selected cut-off dose value, from doses required in respective irradiation locations of the irradiation target body, and thereafter, set a current value of the charged particle beam when the dose distribution is calculated.

2. The treatment planning system according to claim 1, wherein the treatment planning device is configured to set the current value of the charged particle beam when the irradiation target body is irradiated with the charged particle beam, based on the selected cut-off dose value received from the input device, and wherein the treatment planning device is configured to receive the selected cut-off dose value input by the input device in a case where the user selects the cut-off dose value based on content displayed on the display.

3. The treatment planning system according to claim 1, wherein the treatment planning device is configured to automatically select a cut-off dose value, from among the plurality of the cut-off dose values, corresponding to a parameter closest to the parameter received from the input device.

4. The treatment planning system according to claim 1, wherein the treatment planning device acquires one treatment plan, and calculates at least two dose distributions in a case where at least two of the cut-off dose values are adopted for the treatment plan.

5. The treatment planning system according to claim 1, wherein the treatment planning device acquires at least two treatment plans in a case where at least two of the cut-off dose values are adopted, and calculates the dose distribution for each of the treatment plans.

* * * * *